US007358380B2

(12) United States Patent
Kortz et al.

(10) Patent No.: US 7,358,380 B2
(45) Date of Patent: Apr. 15, 2008

(54) RU-SUBSTITUTED POLYOXOMETALATES AND PROCESS FOR THEIR PREPARATION

(75) Inventors: Ulrich Kortz, Bremen (DE); Lihua Bi, Changchun (CN)

(73) Assignee: ExxonMobil Chemical Patents Inc., Houston, TX (US)

( * ) Notice: Subject to any disclaimer, the term of this patent is extended or adjusted under 35 U.S.C. 154(b) by 121 days.

(21) Appl. No.: 11/445,095

(22) Filed: May 31, 2006

(65) Prior Publication Data
US 2007/0282140 A1  Dec. 6, 2007

(51) Int. Cl.
C07F 19/00 (2006.01)
C01G 41/02 (2006.01)
B01J 23/00 (2006.01)
C07C 51/16 (2006.01)

(52) U.S. Cl. .......................... 556/28; 534/11; 534/15; 502/313; 423/593.1; 423/594.13; 562/512.2; 562/545; 562/549

(58) Field of Classification Search ............. 423/593.1, 423/594.13; 502/313; 534/11, 15; 556/28; 562/512.2, 545, 549
See application file for complete search history.

(56) References Cited

U.S. PATENT DOCUMENTS

| 4,839,008 | A | * | 6/1989 | Hill | 204/157.15 |
| 5,091,354 | A | | 2/1992 | Ellis, Jr. et al. | 502/200 |
| 5,475,178 | A | * | 12/1995 | Del Rossi et al. | 585/455 |
| 5,990,348 | A | | 11/1999 | Lyons et al. | 562/549 |
| 6,169,202 | B1 | * | 1/2001 | Wijesekera et al. | 562/549 |
| 7,019,165 | B2 | * | 3/2006 | Davis et al. | 562/480 |
| 7,097,858 | B2 | * | 8/2006 | Hill et al. | 424/604 |
| 2003/0144550 | A1 | * | 7/2003 | Davis et al. | 562/545 |
| 2003/0157012 | A1 | * | 8/2003 | Pope et al. | 423/417 |
| 2004/0185078 | A1 | * | 9/2004 | Hill et al. | 424/402 |
| 2004/0185116 | A1 | * | 9/2004 | Hill et al. | 424/617 |
| 2005/0112055 | A1 | * | 5/2005 | Shannon et al. | 423/594.13 |

FOREIGN PATENT DOCUMENTS

JP  11199594  7/1999
WO  WO 03/028881  4/2003

OTHER PUBLICATIONS

Bi et al., "A novel isopolytungstate functionalized by ruthenium: $[HW_9O_{33}Ru^{II}_2(dmso)_6]^{7-}$," Chem. Commun. 2004, 1420-1421.
Bi et al., "The Ru(II)-supported heptatungstates $[HXW_7O_{28}Ru(dmso)_3]^{6-}$ (X=P, As)," Chem. Commun. 2005, 3962.
Bi et al., "The ruthenium(II)-supported heteropolytungstates $[Ru(dmso)_3(H_2O)-XW_{11}O_{39}]^{6-}$ (X = Ge, Si)," J. Chem. Soc., Dalton Trans. 2004, 3184.

(Continued)

Primary Examiner—Porfirio Nazario-Gonzalez

(57) ABSTRACT

The invention relates to polyoxometalates represented by the formula $(A_n)^{m+}[R_2(H_2O)_6X_2W_{20}O_{70}]^{m-}$ or solvates thereof, wherein A represents a cation, n is the number of the cations, m is the charge of the polyoxoanion, and X represents a heteroatom selected from $Sb^{III}$, $Bi^{III}$, $As^{III}$, $Se^{IV}$ and $Te^{IV}$, a process for their preparation and their use for the catalytic oxidation of organic molecules.

24 Claims, 1 Drawing Sheet

OTHER PUBLICATIONS

Bösing et al., "New Strategies for the Generation of Large Heteropolymetallate Clusters: The β-B-SbW$_9$ Fragment as a Multifunctional Unit," Chem. Eur. J., vol. 3, No. 8, 1997, 1232-1237.

Cavani et al., "Combined effects of Sb-doping and of preparation via lacunary precursor for P/Mo-based, Keggin-type polyoxometalates, catalysts for the selective oxidation of isobutene to metacrylic acid," Topics in Catalysis 2003, 23, 141-152.

Cavani, F., "Heteropolycompound-based catalysts: A blend of acid and oxidizing properties," Catalysis Today 41 (1998) 73-86.

Finke et al., "Is It True Dioxygenase or Classic Autoxidation Catalysis? Re-Investigation of a Claimed Dioxygenase Catalyst Based on a Ru$_2$-Incorporated, Polyoxometalate Precatalyst," Inorg. Chem. 2005, 44, 4175-4188.

Kamata et al., "Efficient Epoxidation of Olefins with ≧99% Selectivity and Use of Hydrogen Peroxide," Science 2003, vol. 300, 964-966.

Laurencin et al., "A new organometallic heterppolytungstate related to [Sb$_2$W$_{22}$O$_{74}$(OH)$_2$]$_{12-}$: Synthesis and structural characterization of the bis-{Ru($p$-cymene)}$^{2+}$-containing anion [Sb$_2$W$_{20}$O$_{70}${Ru($p$-cymene)}$_2$]$^{10-}$," Chemical Communications, vol. 44, 2005, 5524-5526.

Limanski et al., "Syntheses and X-ray characterization of novel tellurium-substituted lacunary polyoxotungstates containing V$^{IV}$, Co$^{II}$, Ni$^{II}$ and Zn$^{II}$ as heteroatoms," Journal of Molecular Structure, vol. 656, No. 1-3, 2003, 17-25.

Loose et al., "Heteropolymetallate Clusters of the Subvalent Main Group Elements Bi$^{III}$ and Sb$^{III}$," Inorg. Chem., vol. 38, 1999, 2688-2694.

Misono et al., "Recent Progress in Catalytic Technology in Japan," Applied Catalysis, vol. 64 (1-2), Sep. 1990, 1-30.

Misono, M., "Unique acid catalysis of heteropoly compounds (heteropolyoxometalates) in the solid state," Chem. Comm., 2001, 1141-1152.

Neumann et al., "Hydroxylation of Alkanes with Molecular Oxygen Catalyzed by a New Ruthenium-Substituted Polyoxometalate, [WZnRu$_2^{III}$(OH)(H$_2$O)(ZnW$_9$O$_{34}$)$_2$]$^{11-}$," Angew. Chem. Int. Ed. Engl. 1995, 34, 1587.

Neumann et al., "Noble Metal (Ru$^{III}$, Pd$^{III}$, Pt$^{II}$) Substituted "Sandwich" Type Polyoxometalates: Preparation, Characterization, and Catalytic Activity in Oxidations of Alkanes and Alkenes by Peroxides," Inorg. Chem. 1995, 34, 5753-5760.

Neumann et al., "Preparation and Characterization of New Ruthenium and Osmium Containing Polyoxometalates, [M(DMSO)$_3$Mo$_7$O$_{24}$]$^{4-}$ (M=Ru(II), Os(II)), and Their Use as Catalysts for the Aerobic Oxidation of Alcohols," Inorg. Chem. 2003, 42 (10), 3331-3339.

Neumann et al., "Molecular Oxygen Activation by a Ruthenium-Substituted "Sandwich" Type Polyoxometalate," J. Am. Chem. Soc. 1998, 120, 11969-11976.

Neumann et al., "A Highly Chemoselective, Diastereoselective, and Regioselective Epoxidation of Chiral Allylic Alcohols with Hydrogen Peroxide, Catalyzed by Sandwich-Type Polyoxometalates: Enhancement of Reactivity and Control of Selectivity by the Hydroxy Group through Metal-Alcoholate Bonding," J. Org. Chem., vol. 68, No. 5, 2003, 1721-1728.

Neumann R., "Polyoxometalate Complexes in Organic Oxidation Chemistry," Progress in Inorganic Chemistry (1998), vol. 47, 317-370.

Nomiya et al., "Synthesis and characterization of a monoruthenium(III)-substituted Dawson polyoxotungstate derived by Br$_2$ oxidation of the 1 : 2 complex of ruthenium(II) and [α$_2$-P$_2$W$_{17}$O$_{61}$]$^{10-}$. The reactivity of cis-[RuCl$_2$(DMSO)$_4$] as a ruthenium source," J. Chem. Soc. Dalton Trans. 2001, 1506-1512.

Pope et al., "Lacunary Polyoxometalate Anions Are π-Acceptor Ligands. Characterization of Some Tungstoruthenate(II,III,IV,V) Heteropolyanions and Their Atom-Transfer Reactivity," J. Am. Chem. Soc. 1992, 114, 2932-2938.

Xu et al., "Studies on Synthesis and Characterization of Noble-metal (Ru)-Substituted Polyoxometalates," Fudan Xuebao, Ziran Kexueban, Journal of Fudan University (Natural Science), vol. 40, No. 4, Aug. 2001, 424-428.

Xu et al., "Studies on the Synthesis and Characterization of Sandwich Type Polyoxometalate (Bu$_4$N)$_7$H$_3$[Ru$_2$O(H$_2$O)$_2$(γ-SiW$_{10}$O$_{36}$)$_2$]," Gaodeng Xuexiao Huaxue Xuebao, Chemical Journal of Chinese Universities, vol. 22, No. 4, 2001, 520-523.

\* cited by examiner

RU-SUBSTITUTED POLYOXOMETALATES AND PROCESS FOR THEIR PREPARATION

FIELD OF THE INVENTION

This invention is directed to new ruthenium-substituted polyoxymetalates, a process for their preparation and their use for the catalytic oxidation of organic molecules.

BACKGROUND OF THE INVENTION

Polyoxometalates (POMs) are a unique class of inorganic metal-oxygen clusters. They consist of a polyhedral cage structure or framework bearing a negative charge which is balanced by cations that are external to the cage, and may also contain centrally located heteroatom(s) surrounded by the cage framework. Generally, suitable heteroatoms include Group IIIa-VIa elements such as phosphorus, antimony, silicon and boron. The framework of polyoxometalates comprises a plurality of metal atoms (addenda), which can be the same or different, bonded to oxygen atoms. Due to appropriate cation radius and good $\pi$-electron acceptor properties, the framework metal is substantially limited to a few elements including tungsten, molybdenum, vanadium, niobium and tantalum.

In the past, there have been increasing efforts towards the modification of polyoxoanions with various organic and/or transition metal complex moieties with the aim of generating new catalyst systems as well as functional materials with interesting optical, electronic and magnetic properties. In particular, transition metal substituted polyoxometalates (TMSPs) have attracted continuously growing attention as they can be rationally modified on the molecular level including size, shape, charge density, acidity, redox states, stability, solubility etc.

For example, Neumann et al. describe the preparation of ruthenium-substituted "sandwich" type polyoxometalate $[WZnRu_2(OH)(H_2O)(ZnW_9O_{34})_2]^{11-}$ as well as its ability to catalyze the oxidation of alkanes and alkenes using hydrogen peroxide and molecular oxygen as the oxygen donor (see: Angew. Chem. Int. Ed. Engl. 1995, 34, 1587; Inorg. Chem. 1995, 34, 5753; and J. Am. Chem. Soc. 1998, 120, 11969). Moreover, Pope et al., J. Am. Chem. Soc. 1992, 114, 2932, disclose the synthesis of the cesium salt of $[PW_{11}O_{39}Ru(H_2O)]^{4+}$ and characterize its oxygen atom transfer reactivity. In all these syntheses, $RuCl_3 \cdot nH_2O$ or $[Ru(H_2O)_6](C_7H_7SO_3)_2$ are used as ruthenium sources.

Nomiya et al., J. Chem. Soc., Dalton Trans. 2001, 1506, discuss the difficulty of making pure Ru-containing POMs and the nonreproducibility of some reported Ru-substituted polyanions.

Recently, the dimethyl sulfoxide (dmso) complex cisRu $(dmso)_4Cl_2$ has become a popular ruthenium(II) source for the synthesis of Ru-substituted POMs. For example, Kortz et al. disclose the preparation and structural characterization of $[HW_9O_{33}Ru_2(dmso)_6]^{7-}$, $[Ru(dmso)_3(H_2O)XW_{11}O_{39}]^{6-}$ (X=Ge, Si) and $[HXW_7O_{28}Ru(dmso)_3]^{6-}$ (X=P, As) (see: Chem. Commun. 2004, 1420; J. Chem. Soc., Dalton Trans. 2004, 3184; and Chem. Commun. 2005, 3962).

However, up to now these $Ru^{II}$, $(dmso)_3$-based anions have not turned out to be very useful for homogeneous or heterogeneous catalytic applications.

Therefore, it is an object of the present invention to provide a ruthenium-substituted polyoxometalate which is useful as catalyst in homogeneous and heterogeneous oxidation reactions of organic substrates. Furthermore, such a Ru-substituted POM should be easy and reproducible to prepare.

Other references of interest include:
Neumann et al., JOC, Vol. 68, No. 5, 2003; Finke et al. Inorg Chem. 2005; Neumann et al., Inorg. Chem. 2003 42(10), 3331-3339; WO 2003/028881; Xu et al., Fudan Xuebao, Ziran Kexueban 2001, 40(4), 424-428; Xu et al., Gaodeng Xuexiao Huaxue Xuebao 2001, 22(4), 520-523; U.S. Pat. No. 5,990,348; Tojima et al., JP 11199594-Mitsubishi; Rong, Diss. Abstr. Int. B 1993, 53(10), 5197; J. Org. Chem. 2003, 68, 1721-1728); Cavani et al. Topics in Catalysis 2003, 23, 141-152); and Kamat et al. Science 2003, 300, 964-966).

SUMMARY OF THE INVENTION

This invention relates to Polyoxometalate represented by the formula

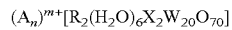

or solvates thereof, wherein
A represents a cation,
n is the number of the cations,
m is the charge of the polyoxoanion, and
X represents a heteroatom selected from $Sb^{III}$, $Bi^{III}$, $As^{III}$, $Se^{IV}$ and $Te^{IV}$.

DETAILED DESCRIPTION OF THE INVENTION

Figure 1:
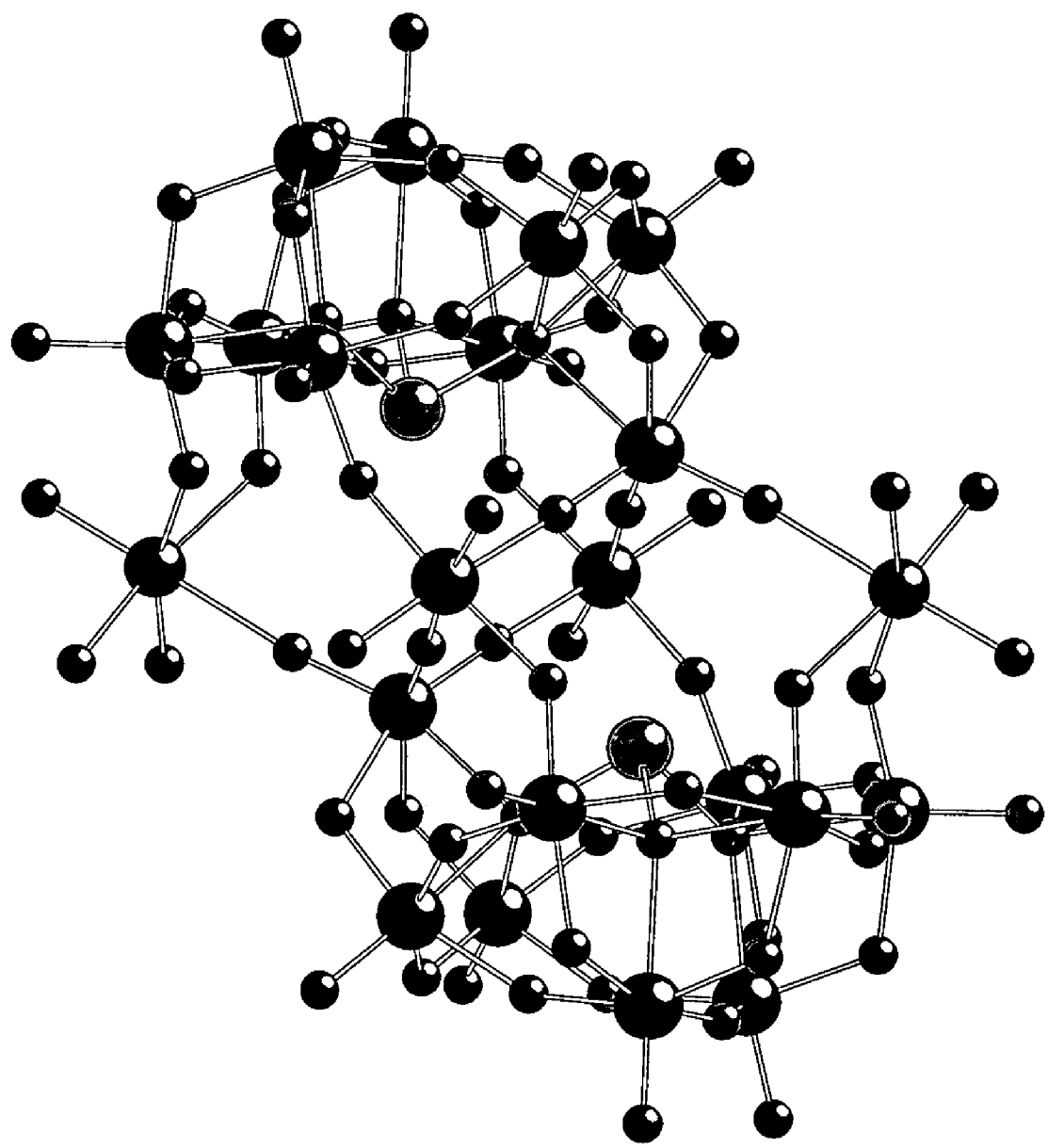
FIG. 1 is an illustration of the structure of the polyanion of example 1.

The CAS numbering scheme for the Periodic Table Groups is used as published in CHEMICAL AND ENGINEERING NEWS, 63 (5), 27 (1985).

The objects described above are achieved by polyoxometalates represented by the formula

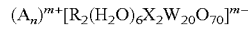

or solvates thereof, wherein
A represents a cation,
n is the number of the cations,
m is the charge of the polyoxoanion, and
X represents a heteroatom selected from $Sb^{III}$, $Bi^{III}$, $As^{III}$, $Se^{IV}$ and $Te^{IV}$.

The polyoxometalates according to the invention are di-Ru containing POMS. The polyanion $[Ru_2 (H_2O)_6 X_2W_{20}O_{70}]^{m-}$ has been found to exist in a Krebs-type structure, i.e. it is a dimeric POM consisting of two trilacunary Keggin fragments B-β-$[XW_9O_{33}]^{p-}$ that are linked by two $\{WO_2\}^{2+}$ and two $\{Ru(H_2O)_3\}^{q+}$ cations.

Each ruthenium is coordinated via three Ru—O—W bonds to the polyanion backbone. The other three coordination sites are each ligated with water. Thus, the present polyoxometalates comprise ruthenium ions having three terminal substitution labile ligands. The structure of preferred polyanions is also illustrated in FIG. 1.

As water ligands can be substituted easily, the polyoxometalates of the invention allow an easy generation of free coordination sites at the catalytically active Ru-atom. Consequently, both ruthenium centers are readily accessible for other ligands including organic substrates and oxygen donor species such as $O_2$, $H_2O_2$, organic peroxides (e.g. t-$(C_4H_9)$ OOH) or peracids (e.g. $CH_3COOOH$) which in turn improves the catalytic performance in oxidation reactions.

The cation A can be one or more Group Ia, IIa, IIIb, IVb, Vb, VIIb, VIIb, VIIIb, Ib, IIb, IIIa, IVa, Va or VIa metal or an organic cation. Preferably, A is selected from the group consisting of lithium, sodium, potassium, rubidium, cesium, magnesium, calcium, strontium, barium, titanium, vanadium, chromium, lanthanum, lanthamide metal, actinide metal, manganese, iron, cobalt, nickel, copper, zinc, ruthenium, palladium, platinum, tin, antimony, tellurium, phosphonium such as tetraalkylphosphonium, ammonium, guanidinium, tetraalkylammonium, protonated aliphatic amines, protonated aromatic amines and combinations thereof. More preferably, A is selected from sodium, potassium, cesium and combinations thereof. In a preferred embodiment A is a combination of sodium and potassium, e.g. $K_4Na_4$.

The number n of cations is dependent on the nature of cation(s) A, namely its/their valence, and the negative charge m of the polyanion which preferably has to be balanced. Typically, the overall charge of all cations A is equal to the charge of the polyanion. In turn, the charge m of the polyanion is dependent on the oxidation states of the heteroatom X and Ru. The oxidation state of Ru comprised in the present polyoxometalates can range from (II) to (V) and preferably is (III). m depends on the oxidation state of the atoms present in the polyanion, e.g., it follows from the oxidation states of W (+6), O (−2), a given heteroatom X (such as +3 for Sb, Bi and As or +4 for Se and Te), and Ru (ranging from +2 to +5, preferably +3). In some embodiments, m is 2, 4, 6, 8, or 10. In some embodiments, n is 1, 2, 3, 4, 5, 6, 7, 8, 9, or 10.

The heteroatom X of the polyoxometalates according to the invention is advantageously selected from $Sb^{III}$ and $Bi^{III}$ and is preferably $Sb^{III}$.

Accordingly, suitable examples of polyoxometalates according to the invention are represented by the formula $$(A_n)^{8+}[Ru_2(H_2O)_6Sb_2W_{20}O_{70}]^{8-}$$

where A and n are as described above.

The invention also includes solvates of the present POMs. A solvate is an association of solvent molecules with a polyoxometalate. Preferably, water is associated with the POMs and thus, the POMs according to the invention can in particular be represented by the formula $$(A_n)^{m+}[R_2(H_2O)_6X_2W_{20}O_{70}]^{m-} \cdot zH_2O,$$

where A, n, X and m are as described above and wherein z represents the number of attracted water molecules per POM molecule, exclusive of the water molecules which are bound as ligand(s) to ruthenium, and mostly depends on the type of cation A (e.g. z could perhaps be about 25 for $Na^+$ cations and about 5 for $K^+$ cations). In some embodiments z is an integer from 1 to 50. In some embodiments, z is 2, 4, 5, 6, 8, 10, 12, 16, 18, 20, 22, 24, 25, 26, or 30.

Suitable examples of the polyoxometalates according to the invention are represented by the formula $$(A_n)^{8+}[Ru_2(H_2O)_6Sb_2W_{20}O_{70}]^{8-} \cdot zH_2O,$$

where A, n, and z are as described above. A particularly referred example is:

$$K_4Na_4[R_2(H_2O)_6Sb_2W_{20}O_{70}] \cdot 12H_2O.$$

The invention is further directed to a process for preparing polyoxometalates according to the invention comprising:

(a) reacting an aqueous solution of a ruthenium precursor comprising at least one ligand Z with
  (i) a salt of $[X_2W_{22}O_{74}(OH)_2]^{w-}$,
  (ii) a salt of $(XW_9O_{33})_{y-}$ and a salt of $WO_4^{2-}$ or
  (iii) an X containing starting material and a salt of $WO_4^{2-}$ to form a salt of $[Ru_2Z_2X_2W_{20}O_{70}]^{x-}$,
(b) optionally isolating the salt obtained in step (a),
(c) heating a solution of the salt obtained in step (a) or (b) in the presence of water to form a salt of $[Ru_2(H_2O)_6 X_2W_{20}O_{70}]^{m-}$,
(d) optionally cooling the reaction mixture of step (c),
(e) optionally adding a salt of A to the reaction mixture of step (c) or step (d) to form $(A_n)^{m+}[Ru_2 (H_2O)_6 X_2W_{20}O_{70}]^{m-}$ or a solvate thereof, and
(f) optionally recovering the polyoxometalate obtained in step (c), (d) or (e), wherein Z is a ligand independently selected from the group consisting of unsubstituted or substituted aryl, unsubstituted or substituted heteroaryl, unsaturated hydrocarbons, ethers, unsubstituted or substituted allyl, aliphatic hydrocarbons, nitriles, carboxylates, peroxides, peracids, CO, $OH^-$, peroxo, carbonate, $NO_3^-$, $NO_2^-$, $NH_3$, amines, $F^-$, $Cl^-$, $Br^-$, $I^-$, $SCN^-$, and $NCS^-$, X is $Sb^{III}$, $Bi^{III}$, $As^{III}$, $Se^{IV}$, $Te^{IV}$, w is the negative charge of the POM-precursor $[X_2W_{22}O_{74}(OH)_2]$ and is 12 for $X=Sb^{III}$, $Bi^{III}$, $As^{III}$ and 10 for $X=Se^{IV}$, $Te^{IV}$, respectively, and y is the negative charge of the POM-precursor $(XW_9O_{33})$ and is 9 for $X=Sb^{III}$, $Bi^{III}$, $As^{III}$ and 8 for $X=Se^{IV}$, $Te^{IV}$, respectively, x is the negative charge of the polyoxoanion obtained in step (a) and is 10 for $X=Sb^{III}$, $Bi^{III}$, $As^{III}$ and 8 for $X=Se^{IV}$, $Te^{IV}$, respectively, and A, n, and m are the same as defined above.

In step (a) a ruthenium precursor is used which comprises at least one ligand Z, which can be selected from the group consisting of unsubstituted or substituted aryl groups, unsubstituted or substituted heteroaryl groups, unsaturated hydrocarbons, ethers, unsubstituted or substituted allyl groups, aliphatic hydrocarbons, nitriles, carboxylates, peroxides, peracids, CO, $OH^-$, peroxo, carbonates, $NO_3$—, $NO_2$—, $NH_3$, amines, $F^-$, $Cl^-$, $Br^-$, $I^-$, $SCN^-$, and $NCS^-$. In case the ruthenium precursor comprises two or more ligands Z, these ligands are independently selected from the above groups. In addition to Z, the ruthenium precursor may also comprise water such as water of hydration. Preferably, Z is selected from the group consisting of benzene, p-cymene, toluene, mesitylene, durene, hexamethylbenzene, 1,3-dimethylimidazolidine-2-ylidene, 2,2'-bipyridine, α- as well as internal olefins with up to 5 carbon atoms such as ethylene, propylene, α-butylene, cis-β-butylene, trans-β-butylene, isobutylene, n-pentylene, and isopentylene, cycloolefins such as cyclooctadiene, tetrahydrofuran, diethyl ether, methyl t-butyl ether and allyl alcohol. Most preferably, Z is p-cymene. Moreover, it is preferred that the Ru precursor is represented by the formula $[ZRuCl_2]_2$ (where Z is as described above), such as $[(benzene)RuCl_2]_2$, $[(p-cymene)RuCl_2]_2$, $[(toluene)RuCl_2]_2$, $[(hexamethylbenzene)RuCl_2]_2$, $[(mesityle) RuCl_2]_2$, and $[(durene)RuCl_2]_2$. In addition, the ruthenium precursor can also be $[Ru(1,3-dimethylimidazolidine-2-ylidene)_4Cl_2]$ or $[Ru(2,2'-bipyridine)_3]Cl_2$.

This Ru precursor is reacted with (i) a salt of $[X_2W_{22}O_{74}(OH)_2]^{w-}$, (ii) a salt of $(XW_9O_{33})_{y-}$ and a salt of $WO_4^{2-}$ or (iii) an X containing starting material, such as $X_2O_3$ or $H_xXO_3$ (e.g. $Sb_2O_3$, $Bi_2O_3$, $H_2SeO_3$) or a salt of $X^{3+}$ or $X^{4+}$, and a salt of $WO_4^{2-}$ to give a di-Ru substituted POM, where the Ru ions are coordinated by Z (X, w, and y, are as described above). It is preferred to react the ruthenium precursor, preferably [ZRuCl$_2$]$_2$(where Z is as described above), with (i) a salt of [X$_2$W$_{22}$O$_{74}$(OH)$_2$]$^{w-}$ and in particular, this reaction is performed in an aqueous solution (where X and w are as described above). Preferably, Sb$^{III}$ is used as X.

It has been found that the course of the reaction of step (a) can be controlled by various parameters such as pH of the solution, reaction temperature, concentration of the starting materials, ionic strength and counterions used.

In a preferred embodiment, the pH of the aqueous solution used in step (a) ranges from 4.8 to 6.5 and preferably from 5.5 to 6.5. Most preferably, a pH of 6.0 is used. Generally, a buffer solution can be used for adjusting the pH. It is particularly preferred to use a sodium acetate buffer having a concentration of 0.5 M and a pH of 6.0 as aqueous solvent. In another embodiment, the concentration of the aqueous solution (preferably a sodium acetate buffer solution) is from 0.1 to 2 M, preferably 0.25 to 1.5 M, preferably from 0.5 to 1.0 M, preferably about 0.5 M).

Furthermore, it is preferred to perform step (a) at a reaction temperature of 50 to 100° C., preferably 60 to 100° C., preferably 80 to 100° C.

In addition, the concentration of the starting materials is considered to have an effect on the reaction of step (a). It is preferred that the concentration of the Ru-precursor, preferably [ZRuCl$_2$]$_2$(where Z is as described above), as well as the concentration of the salt of [X$_2$W$_{22}$O$_{74}$(OH)$_2$]$^{w-}$ (where X and w are as described above) ranges from 4 to 8 mmol/L, preferably 4 to 6 mmol/L. Most preferably, concentrations of about 4 mmol/L are used in step (a).

Suitable salts of the polyanion [X$_2$W$_{22}$O$_{74}$(OH)$_2$]$^{w-}$ (where X and w are as described above) used in step (a) are lithium, sodium, potassium, ammonium and guanidinium. Preferably, the sodium salt of [X$_2$W$_{22}$O$_{74}$(OH)$_2$]$^{w-}$ (where X and w are as described above) is used.

Optionally, the salt of [Ru$_2$Z$_2$X$_2$W$_{20}$O$_{70}$]$^{x-}$ (where Z, X and x are as described above) which is obtained in step (a) can be isolated in step (b). However, such an isolation is not obligatory. In fact, the process of the present invention is preferably performed as a one-pot synthesis without isolation of the intermediate salt of [Ru$_2$Z$_2$X$_2$W$_{20}$O$_{70}$]$_{x-}$ (where Z, X and x are as described above). If it is actually desired to isolate the intermediate, this can be done by bulk precipitation or crystallization with a salt of lithium, sodium, potassium, rubidium, cesium, magnesium, calcium, strontium, barium, titanium, vanadium, chromium, lanthanum, lanthamide metal, actinide metal, manganese, iron, cobalt, nickel, copper, zinc, ruthenium, palladium, platinum, tin, antimony, tellurium, phosphonium such as tetraalkylphosphonium, ammonium, guanidinium, tetraalkylammonium, protonated aliphatic amines, protonated aromatic amines or combinations thereof. More preferably, a sodium, potassium or rubidium salt is used.

In step (c), a solution of the intermediate POM is heated in the presence of water in order to substitute ligands Z (as described above) by water. Preferably, an aqueous solution of [Ru$_2$Z$_2$X$_2$W$_{20}$O$_{70}$]$^{x-}$ (where Z, X and x are as described above) is heated. Furthermore, step (c) is preferably performed at a temperature of 80 to 100° C., preferably 85 to 95° C. Most preferably, the solution is heated to about 90° C. Moreover, the solution of the intermediate is preferably heated for 1 to 120 minutes, preferably 30 to 60 min, more preferably for about 30 min.

In step (d), the heated solution of step (c) can be cooled preferably to room temperature (23° C.) and optionally filtered.

Furthermore, in step (e) a salt of the cation A (as described above) can be added to the reaction mixture of step (c) or step (d) or in case of filtration of the mixture in step (d), to its filtrate. Preferably, the salt of A is added as a solid or in the form of an aqueous solution. The counter-ions of A can be selected from the group consisting of any stable, non-reducing, water soluble anion, e.g. halides, nitrate, sulfate, acetate. Preferably, the chloride salt is used. However, the addition of extra cations A in step (e) is not necessary if the desired cations are already present during step (a), for example as a counter-ion of [X$_2$W$_{22}$O$_{74}$(OH)$_2$]$^{w-}$ (where X and w are as described above) or (XW$_9$O$_{33}$)$_{y-}$ (where X and y are as described above) or a component of the ruthenium precursor.

Isolation of the polyoxometalates according to the invention in step (f) can be effected by common techniques including bulk precipitation or crystallization.

The invention is also directed to the use of polyoxometalates according to the invention for catalyzing homogeneous and heterogeneous oxidation reactions of organic substrates. In particular, the present POMs can be used for oxidizing unsubstituted and substituted hydrocarbons such as branched or unbranched alkanes and alkenes having carbon numbers from C1 to C20, preferably from C1 to C6, cycloalkanes, cycloalkenes, aromatic hydrocarbons or mixtures thereof. Examples of suitable organic substrates are methane, ethane, propane, butane, isobutane, pentane, isopentane, neopentane, hexane, ethylene, propylene, α-butylene, cis-β-butylene, trans-β-butylene, isobutylene, n-pentylene, isopentylene, cyclohexane, adamantane, cyclooctadiene, benzene, toluene, o-xylene, m-xylene, p-xylene, mesitylene, durene, hexamethylbenzene, naphthalene, anthracene, phenantrene and mixtures thereof. Water ligands are substitution labile and therefore the coordination sites of ruthenium are easily accessible to the organic substrate and the oxygen transfer molecule. Consequently, high catalytic activities are achieved. Further, the remarkable thermal stability of the polyoxoxmetalates permits their use under a great variety of reaction conditions.

Prior to their use in oxidation reactions, the present polyoxometalates can be supported on a solid support. Suitable supports include materials having a high surface area and a pore size which is sufficient to allow the polyoxometalates to be loaded, e.g. aerogels of aluminum oxide and magnesium oxide, titanium oxide, zirconium oxide, silica, mesoporous silica, active carbon, zeolites and mesoporous zeolites. In another embodiment, the supported polyoxometalates are further calcined at a temperature not exceeding the transformation temperature of the polyoxometalate, i.e. the temperature at which decomposition of the polyoxometalate starts to take place (usually about 500 to 600° C. for the present POMS).

The supported POMs according to the invention typically have POM loading levels on the support of up to 40 wt. % or even more. Accordingly, POM loading levels on the support of 1 to 40 wt. %, particularly 5 to 30 wt. %, and more particularly 5 to 20 wt. % are in general suitable. POM loading levels can be determined by Inductively Coupled Plasma Mass Spectrometry (ICP) analysis or X-ray photoelectron spectroscopy (XPS). In the event the values from the ICP and XPS differ, the ICP shall control. ICP analysis is performed using a Varian Vista MPX. The samples are prepared using microwave digestion by dissolving 10 mg of the supported POM in a mixture of HNO$_3$ (6 ml), HCl (6 ml), HF (1 ml) and $H_2O_2$ (3 ml). After the first run, 6 ml of boric acid (5%) is added and a second run is performed. The quantification is done by ICP-OES using calibration curves made between 0 and 50 ppm from standards with known amounts of the respective elements. All tests are conducted twice using a 20 mg sample in the second test. The final volume for each sample is 100 ml. XRD analysis is conducted using a Siemens Diffractometer D5000 with Cu K$\alpha$ ($\lambda$=0.15406 nm, 40 kV, 40 mA) radiation, at a scanning speed of 0.06 deg/min. $N_2$ adsorption-desorption isotherms at 77 K are performed with a Quantachrome Autosorb1-C system, the data are analyzed by employing the BJH (Barrett-Joyner-Halenda) method. Pore volume and pore size distribution curves are obtained from the desorption branch of the isotherm. High Resolution TEM (HRTEM) images are obtained with a JEOL 200CX electron microscope operating at 200 kV.

Due to the definite stoichiometry of polyoxometalates, the present POMs can be converted (e.g. by calcination) to mixed metal oxide catalysts in a highly reproducible manner. Consequently, the polyoxometalates according to the invention can also be used as a precursor for mixed metal oxide catalysts such as so-called Mitsubishi-type catalysts which are particularly useful for the oxidation of hydrocarbons such as propane.

This invention further relates to:

1. Polyoxometalate Represented by the Formula

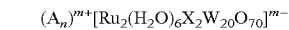

$$(A_n)^{m+}[Ru_2(H_2O)_6X_2W_{20}O_{70}]^{m-}$$

or solvates thereof, wherein

A represents a cation, n is the number of the cations, m is the charge of the polyoxoanion, and X represents a heteroatom selected from $Sb^{III}$, $Bi^{III}$, $As^{III}$, $Se^{IV}$ and $Te^{IV}$.

2. Polyoxometalate according to paragraph 1, wherein A is selected from the group consisting of lithium, sodium, potassium, rubidium, cesium, magnesium, calcium, strontium, barium, titanium, vanadium, chromium, lanthanum, lanthamide metal, actinide metal, manganese, iron, cobalt, nickel, copper, zinc, ruthenium, palladium, platinum, tin, antimony, tellurium, phosphonium, ammonium, guanidinium, tetraalkylammonium, protonated aliphatic amines, protonated aromatic amines and combinations thereof.

3. Process for the preparation of a polyoxometalate according to paragraph 1 or 2 comprising
   (a) reacting an aqueous solution of a ruthenium precursor comprising at least one ligand Z with
      (i) a salt of $[X_2W_{22}O_{74}(OH)_2]^{w-}$,
      (ii) a salt of $(XW_9O_{33})^{y-}$ and a salt of $WO_4^{2-}$, or
      (iii) an X containing starting material and a salt of $WO_4^{2-}$ to form a salt of $[Ru_2Z_2X_2W_{20}O_{70}]^{x-}$,
   (b) optionally isolating the salt obtained in step (a),
   (c) heating a solution of the salt obtained in step (a) or (b) in the presence of water to form a salt of $[Ru_2(H_2O)_6X_2W_{20}O_{70}]^{m-}$,
   (d) optionally cooling the reaction mixture of step (c),
   (e) optionally adding a salt of A to the reaction mixture of step (c) or step (d) to form $(A_n)_{m+}[Ru_2(H_2O)_6X_2W_{20}O_{70}]^{m-}$ or a solvate thereof, and
   (f) optionally recovering the polyoxometalate obtained in step (c), (d) or (e), wherein Z is a ligand independently selected from the group consisting of unsubstituted or substituted aryl, unsubstituted or substituted heteroaryl, unsaturated hydrocarbons, ethers, unsubstituted or substituted allyl, aliphatic hydrocarbons, nitriles, carboxylates, peroxides, peracids, CO, $OH^-$, peroxo, carbonate, $NO_3^-$, $NO_2^-$, $NH_3$, amines, $F^-$, $Cl^-$, $Br^-$, $I^-$, $SCN^-$ and $NCS^-$, w is the negative charge of the polyoxometalate precursor $\{X_2W_{22}O_{74}(OH)_2\}$, y is the negative charge of the POM-precursor $(XW_9O_{33})$, x is the negative charge of the polyoxoanion obtained in step (a), and A, n, m and X are the same as defined in paragraph 1 or 2.

4. Process according to paragraph 3, wherein Z is independently selected from the group consisting of benzene, p-cymene, toluene, mesitylene, durene, hexamethylbenzene, 1,3-dimethylimidazolidine-2-ylidene, 2,2'-bipyridine, $\alpha$- as well as internal olefins with up to 5 carbon atoms, tetrahydrofuran, diethyl ether, methyl t-butyl ether and allyl alcohol.

5. Process according to paragraph 3 or 4, wherein the ruthenium precursor is represented by the formula $[ZRuCl_2]_2$ where Z is as described paragraph 3 or 4.

6. Process according to paragraph 3 or 5, wherein the pH of the aqueous solution used in step (a) ranges from 4.8 to 6.5, preferably from 5.5 to 6.5.

7. Process according to any one of paragraphs 3 to 6, wherein in step (a) a sodium acetate buffer having a concentration of 0.5 M is used as aqueous solvent.

8. Process according to any one of paragraphs 3 to 7, wherein step (a) is performed at a temperature of 50 to 100° C., preferably 60 to 100° C., preferably from 80 to 100° C.

9. Process according to any one of paragraphs 3 to 8, wherein in step (a) the concentration of the ruthenium precursor and the salt of $[X_2W_{22}O_{74}(OH)_2]^{w-}$ ranges from 4 to 8 mmol/L, preferably from 4 to 6 mmol/L, where X represents a heteroatom selected from $Sb^{III}$, $Bi^{III}$, $As^{III}$, $Se^{IV}$ and $Te^{IV}$ and w is as described in paragraph 3.

10. Process according to any one of paragraphs 3 to 9, wherein in step (a) the sodium salt of $[X_2W_{22}O_{74}(OH)_2]^{w-}$ is used where X represents a heteroatom selected from $Sb^{III}$, $B^{III}$, $As^{III}$, $Se^{IV}$ and $Te^{IV}$ and w is as described in paragraph 3.

11. Process according to any one of paragraphs 3 to 10, wherein step (c) is performed at a temperature of 80 to 100° C.

12. Process according to any one of paragraphs 3 to 11, wherein in step (c) the aqueous solution of a salt of $[RuZ_2X_2W_{20}O_{70}]_{x-}$ is heated for 1 to 120 min, preferably 30 to 60 min, where X represents a heteroatom selected from $Sb^{III}$, $Bi^{III}$, $As^{III}$, $Se^{IV}$ and $Te^{IV}$ and Z is as described in paragraph 3 or 4 and x is as described in paragraph 3.

13. Process according to any one of paragraphs 3 to 12, wherein in step (d) the solution of step (c) is cooled and filtered.

14. Process according to paragraph 13, wherein in step (e) a salt of A is added to the filtrate of step (d), where A is as described in paragraph 1 or 2.

15. Process according to any one of paragraphs 3 to 13, wherein in step (f) the product is isolated by bulk precipitation or crystallization.

16. Use of a polyoxometalate according to paragraph 1 or 2 or prepared according to any one of paragraphs 3 to 15 as catalyst for homogeneous or heterogeneous oxidation reactions of organic substrates.

17. Use according to paragraph 16, wherein the organic substrates are unsubstituted or substituted hydrocarbons such as branched or unbranched alkanes and alkenes having carbon numbers from C1 to C20, cycloalkanes, cycloalkenes, aromatic hydrocarbons or mixtures thereof.

18. Use according to paragraph 16 or 17, wherein the polyoxometalate is supported on a solid support.

19. Use according to paragraph 18, wherein the supported polyoxometalate is calcined at a temperature not exceeding the transformation temperature of the polyoxometalate.

20. Use of a polyoxometalate according to paragraph 1 or 2 or prepared according to any one of paragraphs 3 to 15 as a precursor for preparing mixed metal oxide catalysts.

21. Use according to paragraph 20, wherein the mixed metal oxide catalysts are Mitsubishi-type catalysts.

The invention is further illustrated by the following examples.

EXAMPLES

Example 1

Synthesis of $K_4Na_4[Ru_2(H_2O)_6Sb_2W_{20}O_{70}] \cdot 12H_2O$ 0.05 g (0.08 mmol) of [(p-cymene)RuCl$_2$]$_2$ (obtained from Sigma-Aldrich) was dissolved with stirring in 20 mL of 0.5 M NaAc buffer (pH 6.0). Then 0.5 g (0.08 mmol) of $Na_{12}[Sb_2W_{22}O_{74}(OH)_2]$ (synthesized according to Krebs et al., Chem. Eur. J. 1997, 3, 1232) was added. The solution was heated to 90° C. for 30 min and filtered after it had cooled. Then 0.5 mL of 1.0 M KCl solution was added to the filtrate. Slow evaporation at room temperature led to 0.12 g (yield 26%) of a yellow crystalline product after one week.

IR (cm-1): 950, 885 (sh), 863 (sh), 836 (sh), 806, 769, 703, 655, 453, 413 (measured on a Nicolet-Avatar 370 spectrometer using KBr pellets).

Besides IR the product was also characterized by single crystal XRD. The crystal data and structure refinement obtained on a Bruker Kappa APEX II instrument using the SHELXTL software package are shown in the following table.

TABLE 1

Crystal data and structure refinement for $K_4Na_4[Ru_2(H_2O)_6Sb_2W_{20}O_{70}] \cdot 12H_2O$

| | |
|---|---|
| Empirical formula | $H_{36} \cdot K_4Na_4O_{88}Ru_2Sb_2W_{20}$ |
| Formula weight | 5733.02 |
| Temperature | 173(2) K |
| Wavelength | 0.71073 Å |
| Crystal system | Triclinic |
| Space group | P-1 |
| Unit cell dimensions | a = 12.2730(2) Å α= 83.1120(10)° |
| | b = 13.0105(3) Å β= 74.5430(10)° |
| | c = 15.9367(3) Å γ= 74.7640(10)° |
| Volume | 2363.08(8) Å$^3$ |
| Z | 1 |
| Density (calculated) | 4.029 Mg/m$^3$ |
| Absorption coefficient | 25.383 mm$^{-1}$ |

TABLE 1-continued

Crystal data and structure refinement for $K_4Na_4[Ru_2(H_2O)_6Sb_2W_{20}O_{70}] \cdot 12H_2O$

| | |
|---|---|
| F(000) | 2472 |
| Crystal size | 0.288 × 0.076 × 0.04 mm$^3$ |
| Theta range for data collection | 2.10 to 31.14°. |
| Index ranges | −17 <= h <= 16, −18 <= k <= 18, −23 <= l <= 23 |
| Reflections collected | 48756 |
| Independent reflections | 14927 [R(int) = 0.0527] |
| Completeness to theta = 31.14° | 98.0% |
| Absorption correction | Multiscan |
| Max. and min. transmission | 1.000 and 0.476 |
| Refinement method | Full-matrix least-squares on F$^2$ |
| Data/restraints/parameters | 14927/0/315 |
| Goodness-of-fit on F$^2$ | 0.999 |
| Final R indices [I > 2sigma(I)] | R1 = 0.0499, wR2 = 0.1382 |
| R indices (all data) | R1 = 0.0817, wR2 = 0.1587 |
| Largest diff. peak and hole | 4.292 and −1.858 e · Å$^{-3}$ |

The atomic coordinates as well as the equivalent isotropic displacement parameters which are defined as one third of the trace of the orthogonalized U$^{ij}$ tensor are shown in Table 2.

TABLE 2

Atomic coordinates x, y and z (·10$^4$ Å) and equivalent isotropic displacement parameters U(eq) (·10$^3$ Å$^2$) for $K_4Na_4[Ru_2(H_2O)_6Sb_2W_{20}O_{70}] \cdot 12H_2O$.

| | x | y | z | U(eq) |
|---|---|---|---|---|
| W(1) | 2132(1) | 2910(1) | −815(1) | 29(1) |
| W(2) | 2622(1) | 3100(1) | −2957(1) | 34(1) |
| W(3) | −16(1) | 4248(1) | −1710(1) | 31(1) |
| W(4) | 1216(1) | 1713(1) | −4102(1) | 37(1) |
| W(5) | −1403(1) | 2893(1) | −2848(1) | 33(1) |
| W(6) | −563(1) | 263(1) | −2998(1) | 31(1) |
| W(7) | 2526(1) | −779(1) | −2987(1) | 34(1) |
| W(8) | 3786(1) | 480(1) | −1953(1) | 32(1) |
| W(9) | 1963(1) | −1020(1) | −798(1) | 26(1) |
| W(10) | 1161(1) | 1116(1) | 933(1) | 27(1) |
| Sb | 402(1) | 1433(1) | −1474(1) | 23(1) |
| Ru | −2842(1) | 3747(1) | −637(1) | 32(1) |
| O(1SB) | 1208(8) | 2624(7) | −1814(6) | 27(2) |
| O(2SB) | 147(8) | 1580(7) | −2675(6) | 27(2) |
| O(3SB) | 1883(8) | 322(7) | −1824(6) | 30(2) |
| O(1RU) | −3260(20) | 4514(18) | 570(15) | 115(7) |
| O(2RU) | −3190(20) | 5100(20) | −1289(17) | 126(8) |
| O(3RU) | −4440(30) | 3450(20) | −410(20) | 161(11) |
| O(3WR) | −1038(9) | 3693(8) | −876(7) | 34(2) |
| O(5WR) | −2059(9) | 2716(8) | −1705(7) | 37(2) |
| O(9WR) | 2433(10) | −2203(9) | −206(7) | 43(3) |
| O(1T) | 2791(9) | 3274(8) | −109(7) | 37(2) |
| O(2T) | 3658(11) | 3612(10) | −3696(8) | 50(3) |
| O(3T) | −618(10) | 5606(9) | −1703(7) | 42(2) |
| O(4T) | 1810(11) | 1799(10) | −5207(8) | 53(3) |
| O(5T) | −2505(11) | 3765(9) | −3250(8) | 46(3) |
| O(6A) | −1017(8) | 131(7) | −1759(6) | 29(2) |
| O(6T) | −1188(10) | −641(9) | −3300(7) | 43(3) |
| O(7T) | 3186(10) | −1669(9) | −3777(8) | 46(3) |
| O(8T) | 5259(10) | 367(9) | −2076(8) | 45(3) |
| O(9T) | 527(8) | −1066(7) | −820(6) | 30(2) |
| O(10A) | 2640(9) | 942(8) | 873(7) | 35(2) |
| O(10T) | 513(9) | 2075(8) | 1694(7) | 36(2) |
| O(12) | 3055(9) | 3343(8) | −1911(7) | 37(2) |
| O(13) | 974(9) | 4184(8) | −876(6) | 33(2) |
| O(18) | 3118(9) | 1491(8) | −1115(7) | 34(2) |
| O(23) | 1401(9) | 4345(8) | −2678(7) | 38(2) |
| O(24) | 1854(10) | 2693(9) | −3691(8) | 44(3) |
| O(28) | 3416(9) | 1666(8) | −2783(7) | 37(2) |
| O(35) | −610(9) | 3857(8) | −2591(7) | 37(2) |
| O(45) | −217(10) | 2742(9) | −4018(7) | 43(3) |
| O(46) | 331(10) | 665(9) | −4113(7) | 42(2) |
| O(47) | 2297(9) | 552(8) | −3728(7) | 38(2) |

TABLE 2-continued

Atomic coordinates x, y and z ($\cdot 10^4$ Å) and
equivalent isotropic displacement parameters U(eq)
($\cdot 10^3$ Å$^2$) for K$_4$Na$_4$[Ru$_2$(H$_2$O)$_6$Sb$_2$W$_{20}$O$_{70}$]·12H$_2$O.

|       | x         | y         | z         | U(eq)  |
|-------|-----------|-----------|-----------|--------|
| O(56) | −1734(9)  | 1531(8)   | −3061(7)  | 36(2)  |
| O(67) | 941(9)    | −663(8)   | −2895(6)  | 32(2)  |
| O(78) | 3895(9)   | −384(8)   | −2904(7)  | 36(2)  |
| O(79) | 2566(9)   | −1662(8)  | −1983(7)  | 35(2)  |
| O(89) | 3571(9)   | −671(8)   | −1175(7)  | 34(2)  |
| O(110)| 1078(8)   | 2167(7)   | −58(6)    | 29(2)  |
| O(910)| 1541(8)   | −13(7)    | 2(6)      | 29(2)  |
| K(1)  | 3435(3)   | −1255(3)  | 1311(3)   | 51(1)  |
| K(2)  | −959(4)   | 3633(3)   | 858(3)    | 48(1)  |
| Na(1) | −4255(19) | 6919(17)  | −715(14)  | 50(5)  |
| Na(2) | −2850(20) | 3093(18)  | −5523(15) | 54(5)  |
| Na(3) | −400(20)  | 2460(20)  | 3222(17)  | 62(6)  |
| O(1W) | 5199(14)  | −1414(12) | −178(10)  | 69(4)  |
| O(2W) | 400(20)   | 4980(19)  | −4308(16) | 120(8) |
| O(3W) | 4741(19)  | 921(17)   | −4562(14) | 106(6) |
| O(4W) | −1300(20) | 1570(20)  | −5167(17) | 134(9) |
| O(5W) | −2591(10) | 7081(9)   | −1741(7)  | 40(2)  |
| O(6W) | 5420(20)  | 3050(20)  | −2218(17) | 128(8) |

The structure of the polyanion is also illustrated in FIG. 1 which shows that two trilacunary Keggin fragments B-β-[SbW$_9$O$_{33}$]$^{9-}$ are linked by two {WO$_2$}$^{2+}$ (the two middle cations) and two {Ru(H$_2$O)$_3$}$^{3+}$ cations (the two outer cations each having three terminal water ligands).

Example 2

Synthesis of Cs$_8$[Ru$_2$(H$_2$O)$_6$Sb$_2$W$_{20}$O$_{70}$]·8H$_2$O

Example 1 was repeated except that 0.5 g of solid CsCl was added to the filtrate instead of 0.5 mL of a KCl solution. 0.40 g (yield 76%) of a yellow, amorphous precipitate was obtained.

All documents described herein are incorporated by reference herein, including any priority documents and/or testing procedures, except to the extent they are inconsistent with this specification. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

The invention claimed is:

1. A polyoxometalate represented by the formula (A$_n$)$^{m+}$[Ru$_2$(H$_2$O)$_6$X$_2$W$_{20}$O$_{70}$]$^{m-}$ or solvates thereof, wherein
A represents a cation,
n is the number of the cations,
m is the charge of the polyoxoanion, and
X represents a heteroatom selected from Sb$^{III}$, Bi$^{III}$, As$^{III}$, Se$^{IV}$ and Te$^{IV}$.

2. The polyoxometalate of claim 1, wherein A is selected from the group consisting of lithium, sodium, potassium, rubidium, cesium, magnesium, calcium, strontium, barium, titanium, vanadium, chromium, lanthanum, lanthamide metal, actinide metal, manganese, iron, cobalt, nickel, copper, zinc, ruthenium, palladium, platinum, tin, antimony, tellurium, phosphonium, ammonium, guanidinium, tetraalkylammonium, protonated aliphatic amines, protonated aromatic amines and combinations thereof.

3. A process for the preparation of the polyoxometalate of claim 1 comprising
(a) reacting an aqueous solution of a ruthenium precursor comprising at least one ligand Z with
  (i) a salt of [X$_2$W$_{22}$O$_{74}$(OH)$_2$]$^{w-}$,
    a salt of (XW$_9$O$_{33}$)$_{y-}$ and a salt of WO$_4^{2-}$, or an X containing starting material and a salt of WO$_4^{2-}$
    to form a salt of [Ru$_2$Z$_2$X$_2$W$_{20}$O$_{70}$]$^{x-}$,
(b) optionally isolating the salt obtained in step (a),
(c) heating a solution of the salt obtained in step (a) or (b) in the presence of water to form a salt of [Ru$_2$(H$_2$O)$_6$X$_2$W$_{20}$O$_{70}$]$^{m-}$,
(d) optionally cooling the reaction mixture of step (c),
(e) optionally adding a salt of A to the reaction mixture of step (c) or step (d) to form (A$_n$)$^{m+}$[Ru$_2$(H$_2$O)$_6$X$_2$W$_{20}$O$_{70}$]$^{m-}$ or a solvate thereof, and
(f) optionally recovering the polyoxometalate obtained in step (c), (d) or (e),
wherein
Z is a ligand independently selected from the group consisting of unsubstituted or substituted aryl, unsubstituted or substituted heteroaryl, unsaturated hydrocarbons, ethers, unsubstituted or substituted allyl, aliphatic hydrocarbons, nitriles, carboxylates, peroxides, peracids, CO, OH$^-$, peroxo, carbonate, NO$_3^-$, NO$_2^-$, NH$_3$, amines, F$^-$, Cl$^-$, Br$^-$, I$^-$, SCN$^-$ and NCS$^-$,
w is the negative charge of the polyoxometalate precursor {X$_2$W$_{22}$O$_{74}$(OH)$_2$},
y is the negative charge of the POM-precursor (XW$_9$O$_{33}$),
x is the negative charge of the polyoxoanion obtained in step (a), and
A, n, m and X are the same as defined in claim 1.

4. The process of claim 3, wherein Z is independently selected from the group consisting of benzene, p-cymene, toluene, mesitylene, durene, hexamethylbenzene, 1,3-dimethylimidazolidine-2-ylidene, 2,2'-bipyridine, α- as well as internal olefins with up to 5 carbon atoms, tetrahydrofuran, diethyl ether, methyl t-butyl ether and allyl alcohol.

5. The process of claim 3, wherein the ruthenium precursor is represented by the formula [ZRuCl$_2$]$_2$, where Z is as defined in claim 3.

6. The process of claim 3, wherein the pH of the aqueous solution used in step (a) ranges from 4.8 to 6.5.

7. The process of claim 3, wherein in step (a) a sodium acetate buffer having a concentration of 0.5 M is used as aqueous solvent.

8. The process of claim 3, wherein step (a) is performed at a temperature of 50 to 100° C.

9. The process of claim 3, wherein in step (a) the concentration of the ruthenium precursor and the salt of [X$_2$W$_{22}$O$_{74}$(OH)$_2$]$^{w-}$ ranges from 4 to 8 mmol/L, where X represents a heteroatom selected from Sb$^{III}$, Bi$^{III}$, As$^{III}$, Se$^{IV}$ and Te$^{IV}$ and where w is the negative charge of the polyoxometalate precursor {X$_2$W$_{22}$O$_{74}$(OH)$_2$}.

10. The process of claim 3, wherein in step (a) the sodium salt of [X$_2$W$_{22}$O$_{74}$(OH)$_2$]$^{w-}$ is used and where X represents a heteroatom selected from Sb$^{III}$, Bi$^{III}$, As$^{III}$, Se$^{IV}$ and Te$^{IV}$ and where w is the negative charge of the polyoxometalate precursor {X$_2$W$_{22}$O$_{74}$(OH)$_2$}.

11. The process of claim 3, wherein step (c) is performed at a temperature of 80 to 100° C.

12. The process of claim 3, wherein in step (c) the aqueous solution of a salt of [RuZ$_2$X$_2$W$_2$O$_{70}$]$^{x-}$ is heated for 30 to 60 min and where X represents a heteroatom selected from Sb$^{III}$, Bi$^{III}$, As$^{III}$, Se$^{IV}$ and Te$^{IV}$ and Z is a ligand independently selected from the group consisting of unsubstituted or substituted aryl, unsubstituted or substituted heteroaryl, unsaturated hydrocarbons, ethers, unsubstituted or substituted allyl, aliphatic hydrocarbons, nitriles, carboxylates, peroxides, peracids, CO, OH$^-$, peroxo, carbonate, $NO_3^-$, $NO_2^-$, $NH_3$, amines, F$^-$, Cl$^-$, Br$^-$, I$^-$, SCN$^-$ and NCS$^-$, and x is the negative charge of the polyoxoanion obtained in step (a).

13. The process of claim 3, wherein in step (d) the solution of step (c) is cooled and filtered.

14. The process of claim 13, wherein in step (e) a salt of A is added to the filtrate of step (d), where A represents a cation.

15. The process of claim 3, wherein in step (f) the product is isolated by bulk precipitation or crystallization.

16. The polyoxometalate according to claim 1 wherein the polyoxometalate is supported on a solid support.

17. The polyoxometalate of claim 16 wherein the supported polyoxometalate is calcined at a temperature not exceeding the transformation temperature of the polyoxometalate.

18. The polyoxometalate of claim 2 wherein the polyoxometalate is supported on a solid support.

19. The polyoxometalate of claim 18 wherein the supported polyoxometalate is calcined at a temperature not exceeding the transformation temperature of the polyoxometalate.

20. A process to oxidize organic substrates comprising contacting an organic substrate with one or more polyoxometalates of claim 1.

21. The process of claim 20, wherein the organic substrates are unsubstituted or substituted hydrocarbons such as branched or unbranched alkanes and alkenes having carbon numbers from C1 to C20, cycloalkanes, cycloalkenes, aromatic hydrocarbons or mixtures thereof.

22. The process of claim 20 wherein the organic substrate is an alkane.

23. The process of claim 20 wherein the polyoxometalate is supported on a solid support.

24. The process of claim 20 wherein the supported polyoxometalate is calcined at a temperature not exceeding the transformation temperature of the polyoxometalate.

* * * * *